United States Patent [19]

Hill

[11] 4,363,663

[45] Dec. 14, 1982

[54] ANTIMICROBIAL SOLUTION

[76] Inventor: Nicholas J. Hill, 83 Lowell St., Andover, Mass. 01810

[21] Appl. No.: 251,104

[22] Filed: Apr. 6, 1981

Related U.S. Application Data

[63] Continuation-in-part of Ser. No. 50,459, Jun. 20, 1979, abandoned.

[51] Int. Cl.³ .................. A01N 25/02; C08K 3/30; C08K 3/32
[52] U.S. Cl. ............................ 106/18.31; 71/86; 71/103; 424/337; 523/122; 524/126; 524/128
[58] Field of Search .............. 71/86, 103; 106/18.31; 424/337

[56] References Cited

U.S. PATENT DOCUMENTS 3,052,597 9/1962 Johnston ...................... 424/337
3,199,990 8/1965 Tayler ......................... 424/337
3,471,571 10/1969 Harvey ........................ 260/607

Primary Examiner—Stanford M. Levin
Attorney, Agent, or Firm—Thomas N. Tarrant

[57] ABSTRACT

An antimicrobial solution of a microbiologically active organo sulfonyl ethylene dissolved in an organo phosphorus compound selected from the group consisting of organophosphites and organophosphonates.

9 Claims, No Drawings

ANTIMICROBIAL SOLUTION

CROSS-REFERENCES TO RELATED APPLICATIONS

This application is a continuation-in-part of patent application Ser. No. 050,459 filed June 20, 1979, abandoned.

BACKGROUND OF THE INVENTION

1. Field of the Invention

This invention relates to antimicrobial compositions containing organo sulfonyl ethylene compounds and more particularly to antimicrobial solutions of organo sulfonyl ethylene compounds that are compatible with plastic polymers.

2. Description of the Prior Art

To protect polymer compositions from attack by fungi and similar organisms, it is normal to add an antimicrobial compound to the polymeric composition. One class of antimicrobial compounds is organo sulfonyl ethylene compounds. A process for preparing some of these compounds is described in U.S. Pat. No. 3,471,571. Some uses of these compounds as antimicrobials are described in U.S. Pat. Nos. 3,199,990 and 3,052,597.

The same difficulty encountered with many of the more readily available antimicrobials in adding them to plastic polymers has been encountered with the organo sulfonyl ethylene compounds. The problems is an incompatibility that results in a poor blending manifested by what has been described as "blooming" and generally a tendency to separate with the biocide moving to the surface and causing surface defects and loss of the biocide.

SUMMARY OF THE INVENTION

In accordance with the present invention it has been found that organo sulfonyl ethylene compounds can be dissolved in organo phosphorus compounds to form stable liquid solutions. These solutions have been found compatible with plastic polymers and may be blended with them either directly or after first being diluted with suitable plastic modifiers. Thus it is an object of the invention to provide a solution of organo sulfonyl ethylene compounds with organo phosphorus compounds as antimicrobial additives for plastic polymers. Other objects and features of the invention will become apparent upon reading the following disclosure.

DESCRIPTION OF THE PREFERRED EMBODIMENT

The antimicrobial organo sulfonyl ethylenes useful in the composition of this invention are represented by the following formulae:

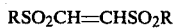

$RSO_2CH{=}CHSO_2R$

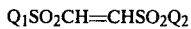

$Q_1SO_2CH{=}CHSO_2Q_2$

In the above formulae R is an alkyl group of 1 to 12 carbon atoms and wherein the compound has the trans configuration. $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

The preferred organo sulfonyl ethylene is trans-1,2-bis (n-prophyl sulfonyl) ethylene.

The liquid organo phosphorus solvents encompassed by the present invention are alkyl phosphites, aryl phosphites, alkyl-aryl phosphites, mono, di, tri and polyphosphites as well as glycol phosphonates. Alkyl phosphites include dioctyl phosphite, triisodecyl phosphites, triisooctyl phosphites, trilauryl phosphite and tris (dipropylene glycol) phosphite. Aryl phosphites include diphenyl phosphite, trisnonylphenyl phosphite, and triphenyl phosphite. Alkyl-aryl phosphites include diphenyl isodecyl phosphite, diphenyl isooctyl phosphite, and phenyl diisodecyl phosphite. Diphosphites include bis (neopentylglycol) triethylene glycol diphosphite, tetrakis (nonylphenyl) polypropylene glycol diphosphite and tetraphenyl dipropylene glycol diphosphite. Tri and polyphosphites include heptakis (dipropylene glycol) triphosphite and poly (dipropylene glycol) phenyl phosphite. By glycol phosphonate is meant bis (dipropylene glycol) dipropylene glycol phosphonate and Di (amyl) amyl phosphonate. These organo phosphorus compounds can also be employed in admixture. The organo sulfonyl ethylene comprises up to about 16 weight percent of the resultant solution.

The organo sulfonyl ethylene-organo phosphite or organo sulfonyl ethylene-organo phosphonate solutions are incorporated into polymeric compositions as such or they can be diluted with plasticizers or other modifiers such that the biocide-solvent or biocide-solvent-diluent solutions contain organo sulfonyl ethylene biocide in amounts of about 2 weight percent to about 10 weight percent. The biocide-solvent or biocide-solvent-diluent solutions are incorporated into polymeric compositions in amounts of about 1 weight percent to about 15 weight percent, preferably about 1 weight percent to about 10 weight percent so that the resulting polymeric composition contains about 0.1 weight percent to about 2.0 weight percent and preferably about 0.1 weight percent to about 1.0 weight percent of organo sulfonyl ethylene.

The organo sulfonyl ethylene solutions of the present invention can be employed in coatings, adhesives and a variety of polymeric compositions such as polyvinyl chloride, vinyl chloride-vinyl acetate copolymer, ethylene vinyl acetate or with polyethylene, polypropylene or polyurethane. They are also valuable in highly dilute solutions as biocidal sprays or baths wherein the organo sulfonyl ethylene is present in percentages substantially less than 1.0 weight percent.

The following examples illustrate the present invention and are not intended to limit the same. Example 1 describes the preparation of thirteen antimicrobial solutions according to the invention.

EXAMPLE 1

The compositions shown in Table I were prepared by first mixing trans-1,2-bis(n-propylsulfonyl) ethylene with organophosphite or organophosphonate. The resultant mixture was then agitated while being heated until the cloudy mixture became clear. The temperature at which trans-1,2-bis(n-propylsulfonyl) ethylene dissolved in a particular organophosphorus compound is shown in Table I. The solutions were cooled to room temperature and allowed to stand for a 16 week period during which the samples were observed for stability. Thereafter, each solution was subjected to a freeze-thaw cycle at −2° C. for 8 hours on a continuous basis for 6 days. All of the solutions shown in Table I remained stable.

The solutions were prepared by making incremented (1% each time) additions of the organo sulfonyl ethylene to establish the upper limits of solubility in the various phosphite and phosphonate solvents. Solutions of 1 and 2 percent were prepared in every case. Lower percentages are inherent.

|  | SAMPLE | | |
|---|---|---|---|
|  | 1 | 2 | 3 |
| Conoco 5305 (PVC resin) | 100.0 | 100.0 | 100.0 |
| Drapex 4.4 (plasticizer) | 5.0 | 1.0 | 5.0 |
| Mark 52 (heat stabilizer) | 2.5 | 2.5 | 2.5 |
| Dioctyl Phthalate (plasticizer) | 46.0 | 50.0 | 50.0 |
| Stearic acid (lubricant) | 0.3 | 0.3 | 0.3 |

TABLE I

| SOLUTION COMPONENT | WEIGHT PERCENT | | | | | | | | | | | | |
|---|---|---|---|---|---|---|---|---|---|---|---|---|---|
| Heptakis(dipropylene glycol)triphosphite | 93 | | | | | | | | | | | | |
| Triisodecyl phosphite | | 90 | | | | | | | | | | | |
| Tris nonyl phenylphosphite | | | 97 | | | | | | | | | | |
| Tris neodal phosphite | | | | 89 | | | | | | | | | |
| Tris dipropylene glycol phosphite | | | | | 84 | | | | | | | | |
| Diphenyl isodecyl phosphite | | | | | | 90 | | | | | | | |
| Tetrakis(nonyl phenyl)polypropylene glycol diphosphite | | | | | | | 97 | | | | | | |
| Di(amyl)amyl phosphonate | | | | | | | | 97 | | | | | |
| Tris 2-ethylhexyl phosphite | | | | | | | | | 89 | | | | |
| Tris dipropyleneglycol phosphite } Triisodecyl phosphite } | | | | | | | | | | 6 / 85 | | | |
| Diphenyl didecyl (2,2,4-trimethyl-1,3 pentanediol) diphosphite | | | | | | | | | | | 86 | | |
| Phenyl diisodecyl phosphite | | | | | | | | | | | | 87 | |
| Poly(dipropyleneglycol)phenyl phosphite | | | | | | | | | | | | | 90 |
| Trans-1,2-bis(n-propylsulfonyl)ethylene | 7 | 10 | 3 | 11 | 16 | 10 | 3 | 3 | 11 | 9 | 14 | 13 | 10 |
| Temperature of clear solution (°C.) | 80 | 100 | 145 | 105 | 105 | 105 | 150 | 100 | 95 | 95 | 105 | 105 | 100 |
| Composition No. | 1 | 2 | 3 | 4 | 5 | 6 | 7 | 8 | 9 | 10 | 11 | 12 | 13 |

Example 2 describes dilution of four Example 1 solutions with modifiers. Plasticizers are used in the Example.

EXAMPLE 2

As shown in Table II the compositions of Table I were admixed with plasticizers at room temperature and agitated to insure a uniform mixture. Dioctylphthalate and expoidized soya oil are plasticizers.

TABLE II

|  | Weight Percent | | | |
|---|---|---|---|---|
| Solution Component | A | B | C | D |
| Composition 2 | 50 | | | |
| Composition 4 | | 60 | | |
| Composition 5 | | | 50 | |
| Composition 6 | | | | 50 |
| Dioctyl phthalate | 50 | | 50 | |
| Epoxidized soya oil | | 40 | | 50 |

After the observation period of 10 weeks all solutions shown in Table II remained clear and free from precipitates of any kind. While dioctyl phthalate and epoxidized soya oil are specified in the table, these are members of the groups, phthalate esters and epoxidized oils respectively. Other members of these groups have similar properties as plasticizers and can be expected to be equally suitable for the present use.

Example 3 describes the blending of two of the diluted solutions of Example 2 in polyvinyl chloride and the resultant resistance to fungus and bacteria.

EXAMPLE 3

Compositions A and D from Example 2 were incorporated in a polyvinyl chloride (PVC) composition which was tested for bacterial and fungal activity. PVC compounds were prepared as follows:

| Composition A | 8.0 | |
| Composition D | | 8.0 |

The above ingredients were milled on a two roll mill at 320° F. for 5 minutes and sheeted off at approximately 25 mils thickness. The biocide level in each of Sample 1 and Sample 2 was 0.25 weight percent. The samples were tested for resistance to fungus and bacteria. The zones of inhibition were measured and compared with the control, Sample 3. In both instances the treated samples were found to be effective in inhibiting the growth of microorganisms. The control sample did not inhibit the growth of microorganisms.

EXAMPLE 4

Two percent by weight of trans-1,2-bis (n-propylsulfonyl) ethylene was admixed with ninety eight percent by weight of trioctylphosphate. With agitation this mixture was heated to 150° C. until the mixture became clear. The trans-1,2-bis (n-propylsulfonyl)ethylene appeared to dissolve but upon cooling crystals formed. The crystals were washed and weighed and the weight was exactly equal to the two percent original addition. Therefore trans-1,2-bis (n-propylsulfonyl) ethylene is not soluble in trioctyl phosphate.

This example bears out the previously recognized general insolubility of organo sulfonyl ethylenes. Other similar examples were tried with other liquid phosphates, liquid adipates, epoxidized oils and other various plasticizers with identical results.

While the invention has been described with respect to specific examples, it is obvious to use other related chemical compositions known to have similar characteristics for the same purposes and it is intended to cover the invention as set forth in the following claims.

I claim:

1. An antimicrobial solution comprising a microbiologically active organo sulfonyl ethylene dissolved in an organo phosphorus compound selected from the group consisting of organo phosphites and organo phosphonates.

2. An antimicrobial solution according to claim 1 wherein the organo phosphorus compared is selected from the group consisting of Heptakis (dipropyleneglycol) triphosphite, Triisodecyl phosphite, Tris neodal phosphite, Trisdipropylene glycol phosphite, Diphenyl isodecyl phosphite.

3. An antimicrobial solution according to claim 2 wherein the organo sulfonyl ethylene is Trans-1,2-bis (n-propyl sulfonyl) ethylene.

4. An antimicrobial solution according to claim 2 wherein the Organo sulfonyl ethylene is represented by one of the Formulae $RSO_2CH=CHSO_2R$, $Q_1SO_2CH=CHSO_2Q_2$, wherein R is an alkyl group of 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

5. An antimicrobial solution according to claim 1 wherein the organo sulfonyl ethylene is represented by one of the formulae $RSO_2CH=CHSO_2R$, $Q_1SO_2CH=CHSO_2Q_2$, wherein R is an alkyl group of 1 to 12 carbon atoms and wherein the compound has the trans configuration and wherein $Q_1$ and $Q_2$ are selected from the group consisting of alkyl having 1 to 12 carbon atoms, phenyl, biphenyl, benzyl, lower alkyl phenyl, chlorophenyl, bromophenyl and nitrophenyl.

6. An antimicrobial solution according to claim 1 mixed with a plastic modifier wherein the modifier is at least 10 percent by weight.

7. An antimicrobial solution according to claim 6 wherein said plastic modifier is a plasticizer.

8. An antimicrobial solution according to claim 7 wherein said plasticizer is selected from the group consisting of phthalate esters and expoxidized oils.

9. An antimicrobial solution according to claim 1 wherein said organo sulfonyl ethylene is at least 3 percent by weight of the solution.

* * * * *